United States Patent [19]

Koyama et al.

[11] Patent Number: 5,101,831
[45] Date of Patent: Apr. 7, 1992

[54] SYSTEM FOR DISCRIMINATING SLEEP STATE

[75] Inventors: Emi Koyama, Osaka; Akihiro Michimori, Nishinomiya; Hiroshi Hagiwara, Katano, all of Japan

[73] Assignee: Matsushita Electric Works, Ltd., Japan

[21] Appl. No.: 729,843

[22] Filed: Jul. 12, 1991

Related U.S. Application Data

[63] Continuation of Ser. No. 437,611, Nov. 17, 1989, abandoned.

[30] Foreign Application Priority Data

Jul. 7, 1989 [JP] Japan ................................ 1-176425

[51] Int. Cl.[5] ...................... A61M 21/00; A61B 5/024
[52] U.S. Cl. .................................... 128/687; 128/716; 600/26
[58] Field of Search ................ 128/731, 732, 733, 687, 128/689, 690, 721, 736, 716; 600/26; 340/575

[56] References Cited

U.S. PATENT DOCUMENTS

| | | | |
|---|---|---|---|
| 4,228,806 | 10/1980 | Lidow | 128/731 |
| 4,725,824 | 2/1988 | Yoshioka | 340/575 |
| 4,757,825 | 7/1988 | Diamond | 128/722 |
| 4,776,345 | 10/1988 | Cohen et al. | 128/731 |

Primary Examiner—William E. Kamm
Assistant Examiner—Kevin Pontius
Attorney, Agent, or Firm—Leydig, Voit & Mayer

[57] ABSTRACT

A system for discriminating sleep state of human body provides variation indexes representing variation of the biological signal on the basis of first variation amount denoting a tendency of increment in time series of measured biological signal from the starting time of the measurement and second variation amount denoting the temporal variation of the biological signal, and discriminates different sleep state on the basis of distribution density of the variation indexes exceeding a predetermined threshold, whereby NREM and REM sleep periods in particular can be reliably discriminated, to be sufficiently contributive to a transmission of sleep information that ensures a comfortable awakening.

7 Claims, 5 Drawing Sheets

SYSTEM FOR DISCRIMINATING SLEEP STATE

This application is a continuation of application Ser. No. 07/437,611, filed Nov. 17, 1989, abandoned.

TECHNICAL BACKGROUND OF THE INVENTION

This invention relates to a system which estimates the human sleep state over the entire bedtime on the basis of such biological signals as pulse rate, respiration rate and so on.

The system of the kind referred to can effectively contribute to assurance of optimum or good quality sleep or the like purpose through a discrimination of the sleep state at a preliminarily set time and a determination of optimum wake-up time in response to the discriminated sleep state, etc.

DESCRIPTION OF THE RELATED ART

It is well known that the human sleep state is generally non-uniform and composes a REM/NREM cycle of rapid eye movement (REM) sleep and non-rapid eye movement (NREM). This cycle is repeated periodically, generally at a cycle of 80 to 120 minutes. In normal sleep, each such cycle involves a change of sleep state from a relatively shallow sleep state shifts to a relatively deep sleep state. The shallow sleep state appears again after a continuation of the deep sleep state and thereafter the REM sleep appears. Here, the REM sleep represents a period in which the sleep has different characteristics with respect to that in the NREM sleep. It is regarded to be the state after which a human can smoothly shift to an awakening state from natural sleep. In other words, it is considered optimum that the human wakes up in several minutes immediately after the REM sleep, i.e., in an awakening period.

Recently, there have been suggested various attempts of achieving a comfortable awakening state based on the foregoing variation in the sleep. For example, Japanese Patent Application Laid-Open Publication No. 63-205592 of H. Masaki discloses an alarm clock which obtains as data a required time for the pulse rate to reach a certain unit number. The alarm clock analyzes so as to discriminate between REM sleep and a change of sleep state and to obtain the awakening state by means of a proper alarm signal. According to this alarm clock, the awakening signal can be prevented from being generated during the NREM sleep, so as to avoid forcibly waking up the user with the alarm signal generated while the user is in the relatively deep sleep state of the NREM sleep. However, an abrupt waking-up even during the REM sleep may still cause the user to feel uncomfortable. The clock of H. Masaki only discriminates between REM sleep. Thus, the problem remains in providing the highly comfortable awakening, most probably due to the failure to discriminate a highly precise state of the sleeping.

U.S. Pat. No. 4,228,806 of D. Lidow also discloses a wake-up alarm device which discriminates the shallow sleep from the deep sleep with the electroencephalogram (EEG) activity and pulse rate. An alarm signal generated during the shallow sleep. In practice, however, the alarm signal generation may occur in the REM sleep. Thus substantially the same problem with the foregoing alarm clock by Masaki is left unsolved. Yet, the arrangement of Lidow in which the EEG is employed for discriminating the sleep state of the user, inherently requires that EEG sensor electrodes to be placed on the user's head. While the discrimination may be improved in the accuracy, the use of the device is so annoying to the user to render the device unsuitable for private or home use but acceptable only for the use in hospitals for treatment of sleep disorders. Also the EEG measuring and data processing devices are large in size and rather expensive.

In Japanese Patent Application Laid-Open Publications No. 63-19161 of I. Mihara et al, No. 63-82673 of K. Araki et al and No. 63-150047 of M. Kitado et al, further, suggest various measures for achieving smooth awakening and to fall asleep by means of the pulse rate measurement or EEG analysis.

In any one of these publications, however, there still not been suggested to provide effective devices for comfortable awakening by reliably estimating the NREM and REM sleeps with such biological signals as the easily detected pulse rate or even respiration rate or body temperature measured with emitted ultrared rays from the human body, and so on.

FIELD OF TECHNOLOGY

A primary object of the present invention is, therefore, to provide a system for highly precise discrimination of the sleep state, in particular, the REM and NREM sleep state with a simple and inexpensive arrangement that obtains required information for discrimination on the basis of pulse rate, and for of providing comfortable awakening.

According to the present invention, this object can be realized by a system for discriminating the sleep state, wherein an easily available signal of human body per unit time set by a measuring time setting means is measured by a measuring means to obtain a biological signal. A variation in the biological signal is computed by a variation computing means, and the NREM sleep and any other sleeps are discriminated by a sleep state discriminating means on the basis of the variation in the biological signal. The variation computing means provides variation indexes denoting variation tendency of the biological signal on the basis of the variation amount showing a tendency of increment in time series of measured value of the biological signal from a starting time of the measurement. A sleep state discriminating means discriminates the states of the sleep on the basis of distribution density of the variation indexes which exceed a predetermined threshold.

Other objects and advantages of the present invention shall be made clear in following description of the invention detailed with reference to an embodiment of the invention shown in accompanying drawings.

While the present invention shall now be explained with reference to the embodiment shown in the following drawings, it will be readily appreciated that the intention is not to limit the invention only to the embodiment shown, but rather to include all alteration, modifications and equivalent arrangements possible within the scope of appended claims.

DISCLOSURE OF PREFERRED EMBODIMENT

Figure 1:
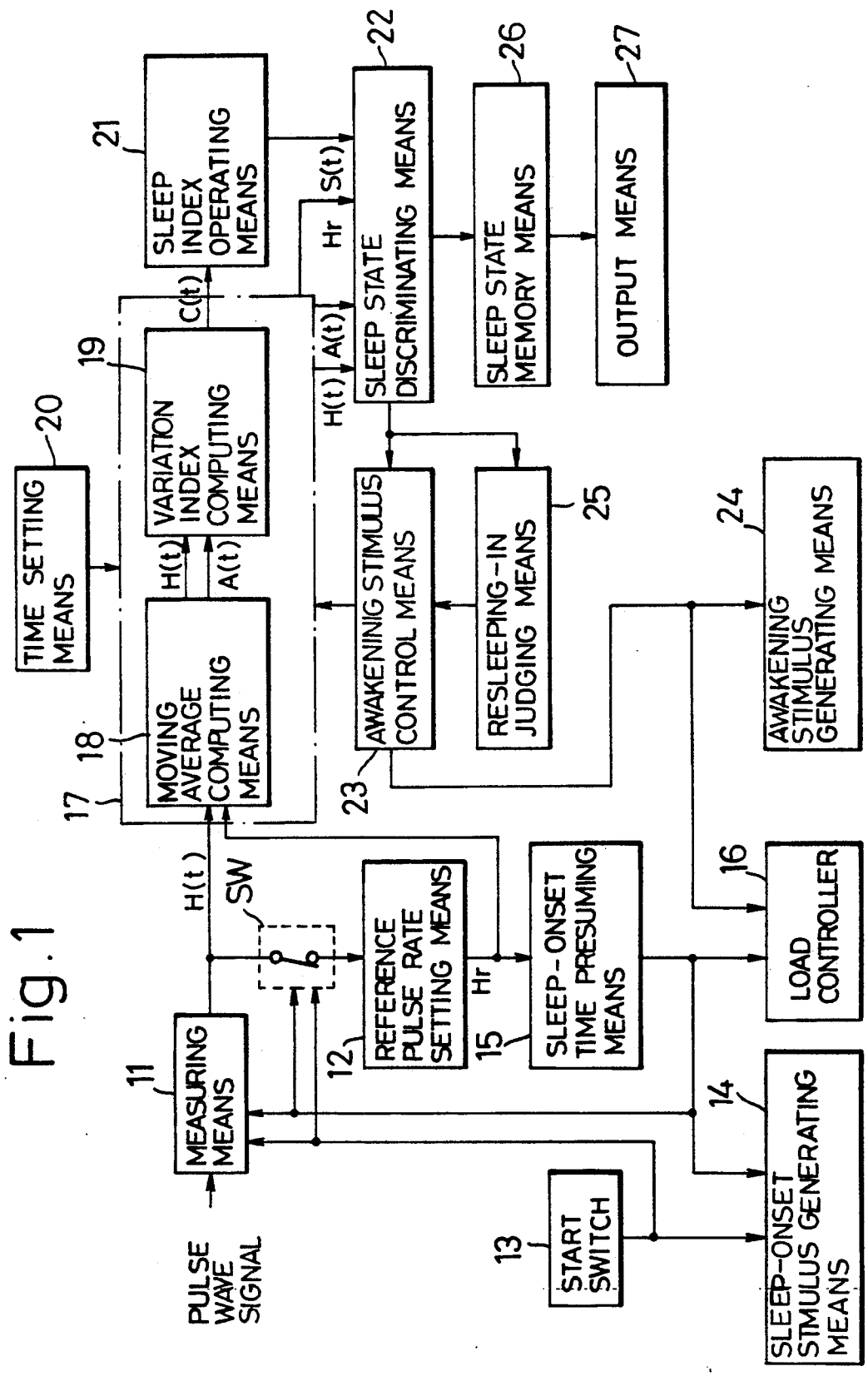
FIG. 1 is a block diagram showing the system for discriminating the sleep state according to the present invention.

Referring here to FIG. 1 showing the system for discriminating the sleep state according to the present invention, a measuring means 11 receives as an input a pulse wave signal from a pulse wave sensor (not shown). For this pulse wave sensor, for example, a photosensor which detects variation in blood flow at a finger tip, ear lobe or the like based on light reflectance or transmission property may be employed. The detection signal is transmitted by means of a wire transmission or wireless transmission with frequency modulation to the measuring means 11, where a pulse curve of the received signals is shaped into a pulse wave and a value of count for every unit time is provided as output data. While the unit time is mainly set to be one minute, the data for every 30 seconds as a unit time are employed by the time when the user is presumed to begin to sleep. The thus obtained pulse rate H(t) includes certain noise component due to body movement or the like but may be deemed employable without hindrance to obtain the trend of variation in the pulse rate.

The pulse rate H(t) is provided through a switching element SW into a reference pulse rate setting means 12 forming a reference value setting section. The switching element SW is controlled by a start signal provided upon operation of a start switch 13 and the switching element SW is set to be ON state by operating the start switch 13 when the measurement is to be started. The start signal is also provided to the measuring means 11 and to means 14 for generating a stimulus for helping the user to fall asleep. At the measuring means 11, the unit time is set to be 30 seconds, and the stimulus generating means 14 operates to give the stimulus proper for helping the user to start feeling sleepy and falling asleep. That is, the stimulus generating means is arranged to generate such stimulus effective to promote the user's shift to the state of asleep as a sound stimulus of a slow and sleepy music that fades out in several minutes, an aromatic stimulus containing a component considered effective for sedative action (such as a fragrance of lavender), vibratory stimulus, optical stimulus, or the like alone or in combination.

Figure 2:
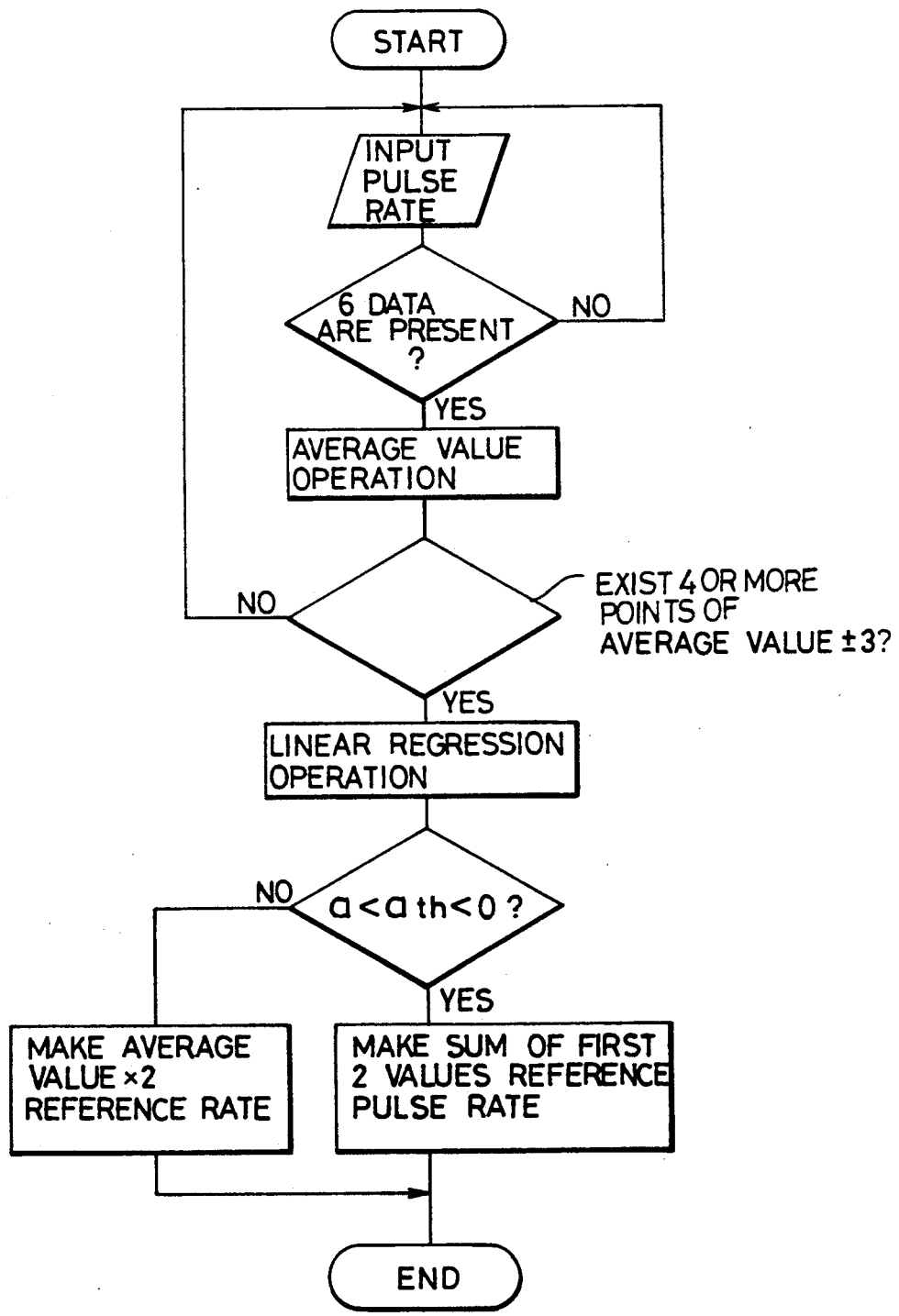
FIG. 2 is a flow chart of the operation at a means for setting a reference pulse rate in the system of FIG. 1.
Figure 3:
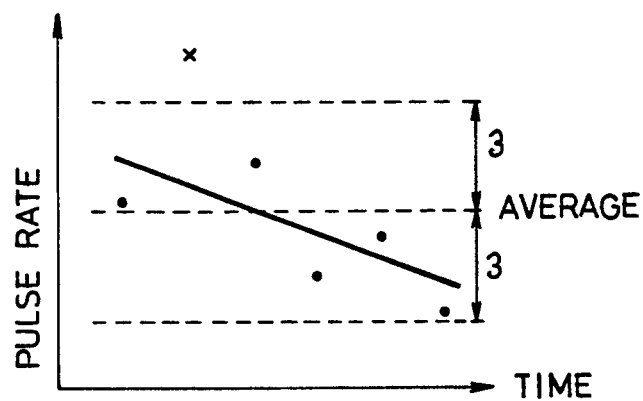
FIG. 3 is a diagram for carrying out a regression analysis in the system of FIG. 1.

The reference pulse-rate setting means 12 carries out such a processing as shown in a flow-chart of FIG. 2 to remove any noise, i.e., an artifact, and determines a reference pulse rate Hr which can be regarded as a pulse rate during resting and awakening state from the bedrest time to the sleep-onset time, as a reference value. Therefore, in the reference pulse-rate setting means 12, six of the pulse rate H(t) provided out of the measuring means 11, that is, its outputs for every 3 minutes are operated in one lump. When a state in which more than four points of less than ±3 with respect to an average value for the six pulse rate values are present, the user is determined to be in a resting state. A regression operation is carried out with remaining values after removal of the values exceeding ±3 with respect to the average value (see FIG. 3). That is, a regression line from linear regression analysis represents a trend of variation in the pulse rate H(t) with respect to the time elapsed. When a regression coefficient a denoting the slope of the regression line satisfies a condition a<a-th<0 wherein a-th is a set negative threshold, it is discriminated that the pulse rate H(t) is decreasing, and a sum of first two of the values below ±3 with respect to the foregoing average value of the data subjected to the regression operation is made to be the reference pulse rate Hr. When the above condition is not satisfied, a value obtained by multiplying the foregoing average value by 2 is made to be the reference pulse rate Hr. In this way, the reference pulse rate Hr is determined as a pulse rate per one minute at a time when less variation is acknowledged in the pulse rate H(t) sequences. That is, the reference pulse rate Hr is to be set at a time point where the pulse rate H(t) has become stable as based on a knowledge that the pulse rate H(t) is stabilized during the resting and awakening state.

The reference pulse rate Hr thus corresponding to the pulse rate during the resting and awakening state and provided out of the reference pulse-rate setting means 12 is provided to a sleep-onset time presuming means 15, where a value of 80 to 95%, for example, 93% of the reference pulse rate Hr is set as a threshold. In the sleep-onset time presuming means 15, thereafter, the pulse rate H(t) signals are subjected to the same processing as in the reference pulse-rate setting means 12 to discriminate whether or not the pulse rate H(t) is in the decreasing period. In an event where the pulse rate H(t) detected during the decreasing period becomes below the threshold, it is discriminated that the user has started to sleep at this moment, and the means 15 provides a sleep-onset signal. The switching element SW is turned OFF when this sleep-onset signal is generated, and the unit time for counting the pulse rate at the measuring means 11 is altered from 30 seconds to 1 minute. The sleep-onset signal stops the operation of the sleep-onset stimulus generating means 14 and also turns a load control means 16 OFF. This load control means 16 is operated for ON and OFF controlling of an external load and is before sleep set in ON state but is turned OFF upon receipt of the sleep-onset signal, whereby any of TV receiving set, luminair and the like electric devices employed as the external load will be turned off.

The pulse rate H(t) and the reference pulse rate Hr obtained as in the foregoing are provided into a variation index operating means 17, which comprises a moving average computing means 18 and a variation index computing means 19. The former obtains a moving average A(t) of the pulse rate H(t) and the latter obtain a variation index C(t) on the basis of the pulse rate H(t) and moving average A(t). In the present instance, the moving average computing means 18 stores the pulse rates H(t) per 1 minute as received from the measuring means 11 and sequentially computes the moving average with a time interval of $\tau$ minutes ($\tau=5$, for example) set before and after respective time points. That is, when the computation is carried out in real time, a moving average at a time $\tau$ minutes before the time point of the computation. Since the pulse rates H(t) for every 30 seconds are provided out of the measuring means 11 prior to the generation of the sleep-onset signal, the variation index computing means 19 carries out an addition of every two of the pulse rates H(t) until the generation of the sleep-onset signal to obtain the pulse rate H(t) per every unit of time.

In respect of central value for computing the moving average, differences from all other values within a range to which the moving average is computing are taken and, when the number of the values the difference of which exceeds a predetermined threshold $\epsilon$ ($\epsilon=3$, for example) is more than 70% of the number of the values within the range for computing the moving average, the value is removed representing as an abnormal value. That is, when any abnormal value is present during computing the moving average, the average value from which any abnormal value is removed is to be employed as the moving average. Any influence on the moving average of an abrupt variation from noise due to the user's body movement or the like can be removed. Further, when the value at the time when the moving average is obtained is an abnormal value, a linear interpolation between a pair of non-abnormal values which are the closest before and after the particular time is carried out and the moving average is replaced by this value obtained through the linear interpolation. The moving average cannot be obtained for a period of $2\tau$ minutes from the starting time and, during this period, the moving average values are computed approximatively where the reference pulse rate Hr provided out of the reference pulse rate setting means 12 is defined as an initial value of the moving average.

On the other hand, the system is so arranged as to be able to discriminate the sleep state at fixed time intervals from the starting time to the wake-up time, depending on the manner in which the time setting means 20 is set. The system in the present instance is started by the operation of the start switch 13 as has been partly referred to, upon which the wake-up time measuring point is preliminarily set by a time setting means 20. In the present instance, the measurement of the sleep state from the starting time is carried out at least once during the user's sleep period and, provided that the intended wake-up time is made Tw and the discrimination time interval is made Ti, then the sleep state is to be discriminated at a measuring time $$tn = Tw - n.Ti (n=1,2 \ldots N).$$

In other words, the discrimination of the sleep state is to be started ahead by a time n.Ti with respect to the set wake-up time Tw. The time interval Ti is set to be an integer multiple of a unit time set by the measuring means 11, and the smallest unit will be 1 minute, i.e., the unit time. At every discriminating time tn, the computation at the variation index computing means 19 is carried out with the pulse rate H(t) and moving averages A(t) obtained from the starting time to the discriminating time tn, and the discrimination of the sleep state is carried out as follows.

Figure 4:
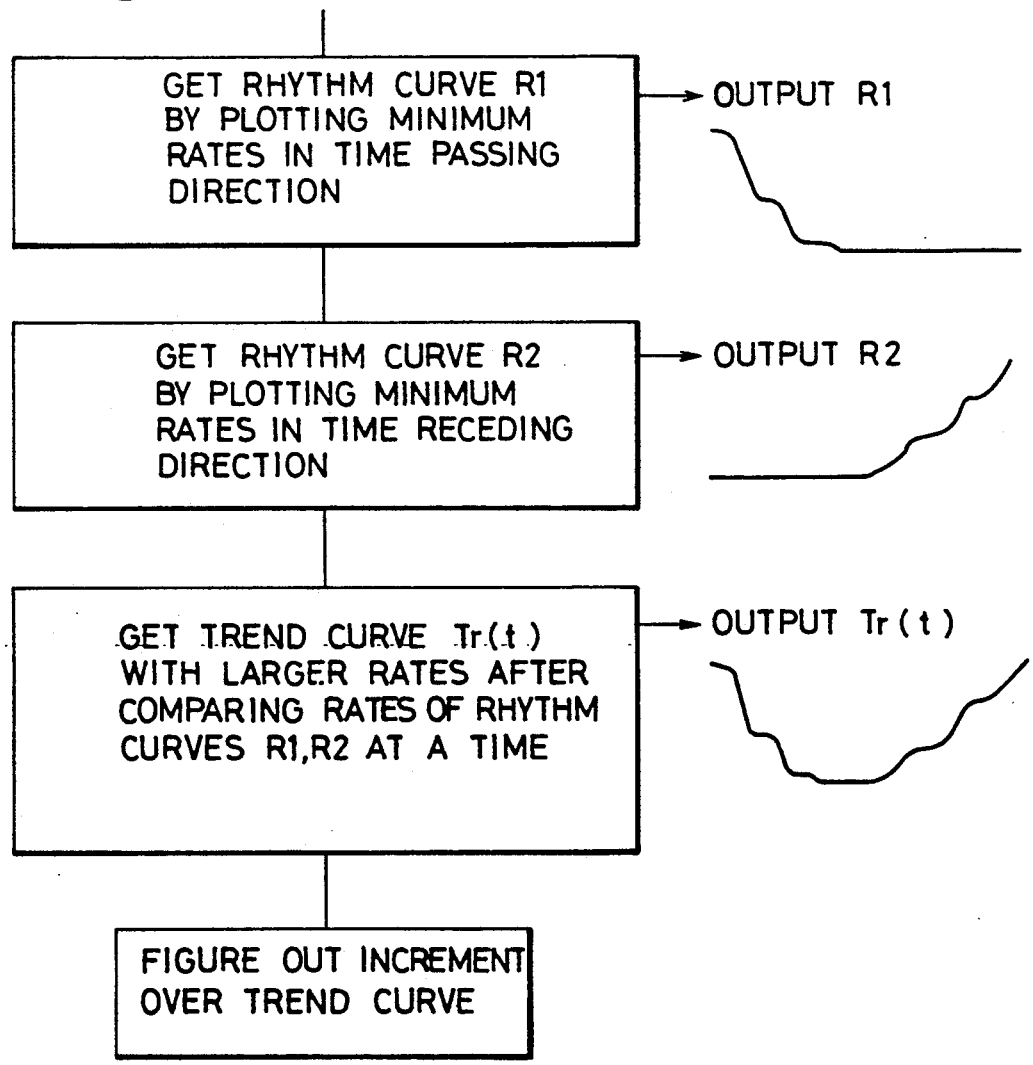
FIG. 4 is a flow chart showing a part of an operation at a variation index computing means in the system of FIG. 1.
Figure 5:
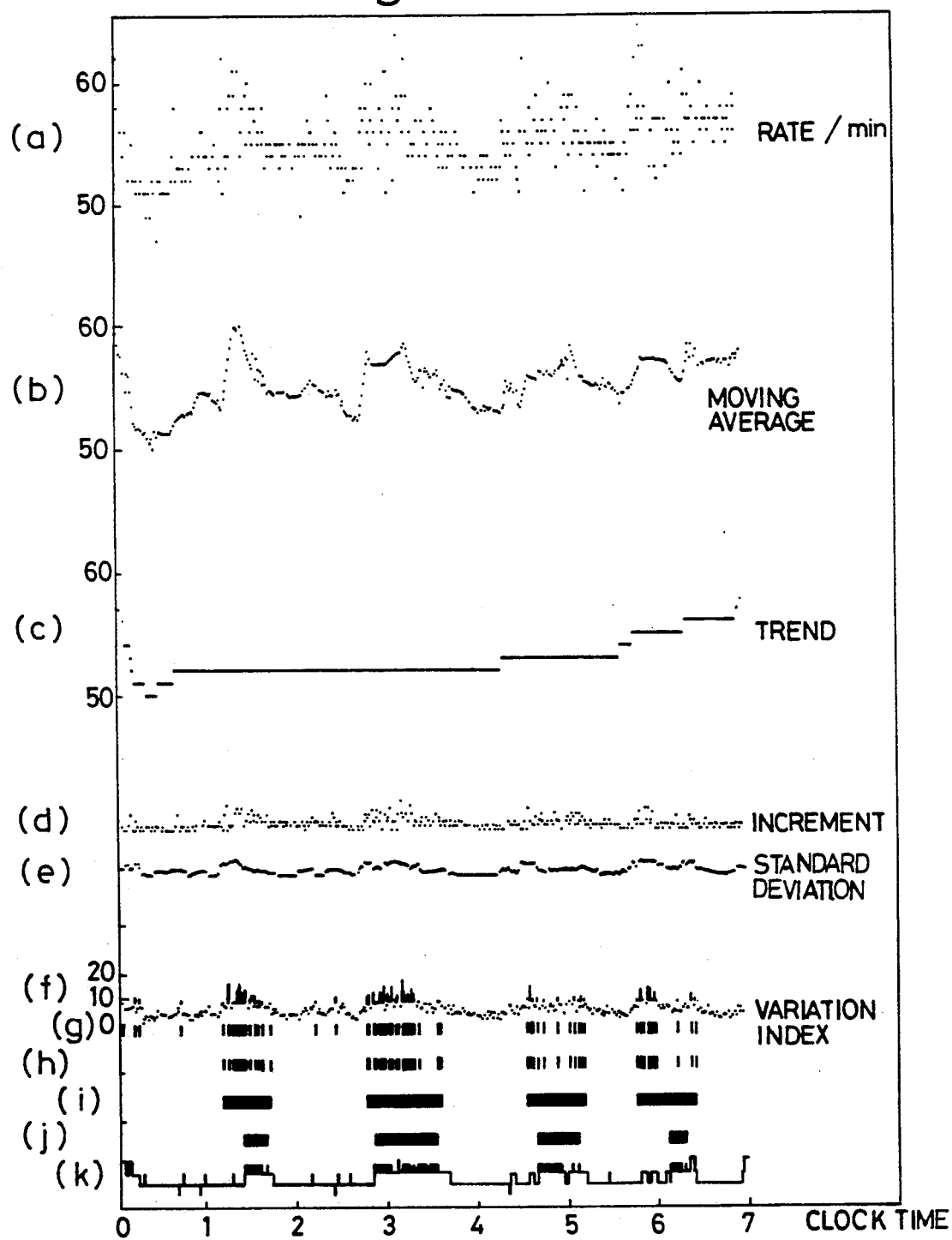
FIG. 5 is a diagram for the discrimination of the sleep state in the system of FIG. 1.

More specifically, also with reference to FIGS. 4 and 5, the variation index computing means 19 obtains first a trend line Tr(t) denoting a trend of the temporal change of the H(t) sequences on the basis of the moving average A(t). This trend line Tr(t) is the one obtained in such that a first rhythm curve R1 is obtained with the minimum values of the moving average at every predetermined unit time in respect of passing direction of time, a second rhythm curve R2 is obtained with the minimum values of the moving average at every predetermined unit time in respect of receding direction of time and the larger value between the first and second rhythm curves R1 and R2 at each time is plotted as a point of the line Tr(t). Then the obtained trend line Tr(t) is compared with the pulse rates H(t) provided out of the measuring means 11, in respect of the size, and an increment I(t) of the pulse rate H(t) with respect to the trend line Tr(t) is represented as in a following expression:

$$I(t) = H(t) - Tr(t) \quad \ldots \text{ when } H(t) \geq Tr(t), \text{ and}$$
$$I(t) = 0 \quad \ldots \text{ when } H(t) < Tr(t).$$

Further, the mean square root D(t) of a difference of the pulse rate H(t) from the moving average A(t) within a range of $\tau$ minutes before and after the respective time t (i.e., a standard deviation in such range) is obtained in a manner of following expression:

$$D(t) = [\Sigma\{H(t+j) - A(t)\}^2/(2\tau+1)]^{\frac{1}{2}}$$

where $[j+ -\tau, \tau]$ and $0 \leq t+j \leq tn$. The variation index C(t) is obtained as (a) linear combination of the obtained increment I(t) and standard deviation D(t) as in a following expression:

$$C(t) = a1.I(t) + a2.D(t)$$

Since, the increment I(t) shows a larger difference between individuals than the standard deviation D(t), both weight a1 and a2 are so set as to satisfy a condition $a1 < a2$. An output attained with $a1=1$ and $a2=2$ for example is shown by a graph (f) in FIG. 5, in which graphs (a)-(e) represent the pulse rate H(t), moving average A(t), trend line Tr(t) and standard deviation D(t), respectively. In this case, the pulse rate H(t) shows smaller temporal variation in the NREM sleep so that the variation index C(t) (graph (f) in FIG. 5) will also be small, while the pulse rate H(t) is larger in the REM sleep or awakening state so that the variation index C(t) will also be larger. In other words, the variation index C(t) is an index into which the increment and decrement and the temporal variation as well are combined, and the NREM and REM sleeps can be discriminated from each other in accordance with the magnitude of the variation index C(t).

Therefore, the variation index C(t) is compared with a threshold Cth set in a sleep index operating means 21. That is, a sleep index S(t) is set by means of the magnitude of the variation index C(t) with respect to the threshold Cth, upon which the sleep index S(t) is defined as in a following expression:

$$S(t) = 1 \ldots \text{ when } C(t) \geq Cth, \text{ and}$$
$$S(t) = 0 \ldots \text{ when } C(t) < Cth.$$

Here, the threshold Cth is so set that the variation indexes C(t) are sequentially arranged from the largest one to the smallest one and 20% of the upper larger ones will be S(t)=1. In other words, S(t)=1 is assigned to the upper 20% of the variation indexes C(t), while S(t)=0 is assigned to the lower 80%. Such setting of the threshold Cth is based on a knowledge that, as in the foregoing, the variation indexes C(t) correspond to the sleep state in such that the period showing the larger variation indexes C(t) corresponds to the REM sleep, and that the REM sleep occupies about 20% of the entire sleep period in normal sleep in the night time.

The sleep indexes S(t) obtained in the foregoing manner are distributed, for example, as in graph (g) of FIG. 5, in which the points of S(t)=1 are shown by black lines, and the FIG. 5 shows that the period of higher distribution density of the black lines of S(t)=1 corresponds to the appearance of the REM sleep and awakening periods. That is, whether the user is in the NREM sleep period, the REM sleep period or in the awakening period is discriminated in a following manner. First, respective points where S(t)=1 are sequentially reviewed in the passing direction of time, intervals of k minutes are set before and after each of such points, the points of S(t)=1 but present only less than m points representing S(t)=1 in such sections are regarded to be isolated points, and they are made to be of a value 0 (graph (h) in FIG. 5). In respect of the remaining set of points, all points of S(t)=0 but present to be less than n between adjacent pair of the points of S(t)=1 are made to be of a value 1. Here, an output example of the sleep index operating means 21 when it is set that k=15, m=3 and n=15 is shown in graph (i) of FIG. 5. Through such processing, continuous black line portions are obtained and such portions are discriminated to be periods in which both the REM sleep and awakening are included.

The pulse rate H(t), reference pulse rate Hr, moving average A(t) and sleep index S(t) which have been obtained in the foregoing manner are provided into a sleep state discriminating means 22, where the sleep states from the starting point to the measuring time tn will be classified on the basis of the sleep index S(t) provided as an output from the sleep index operating means 21, in which a period showing the sleep index S(t) of 0 is discriminated as NREM sleep period and, in a period where St=1, the pulse rate H(t) or the moving average A(t) within this period is compared with the reference pulse rate Hr and, when the reference pulse rate Hr is larger than more than one half of the values in the particular period, the same is discriminated to be REM sleep or the awakening state when the reference pulse rate Hr is smaller. The sleep index S(t) is made to be 1 for the REM sleep period, and to be 2 in the awakening period. Further, a period within a predetermined time $T_R$ after the termination of the REM sleep period (for example, 10 minutes) is regarded as an immediately after REM sleep period. Through these processings, the period of the sleep index S(t) as provided from the sleep index operating means 21 is classified to be the REM sleep (S(t)=1) and awakening periods (S(t)1=2), while the periods of S(t)=0 are classified to be those immediately after REM sleep period and NREM period.

A comparison of the result of discrimination of the sleep state on the basis of the pulse rate as obtained in accordance with the foregoing procedure with a result of visual scoring by means of polysomnograph has proved that they are consistent with each other at a rate of more than 85%. This correspondence may be regarded as being considerably high in view of the fact that even visual scoring by a plurality of specialized doctors in the particular field by means of the polysomnograph reaches only about 90%. Thus, the system according to the present invention is very useful.

At an awakening stimulus control means 23, the time or intensity of an awakening stimulus to be given to the user, is set on the basis of the sleep state sequences. That is, provided that n=N, N-1, ... 1 in the foregoing measuring time Tn (=Tw-n.Ti), N.Ti is the maximum allowance for advancing the awakening time. The sleep state is measured at every time interval Ti after the time Tw-N.Ti (=Tp). Provided here that the unit time for computing the pulse rate H(t) in the measuring means 11 during the sleep is Tu (1 minute in the foregoing example), it is set that $Tu \leq Ti \leq T_R$. Conducting the discrimination of the sleep state at every time interval Ti between the time Tp and the time Tw, it is possible to attain a result among such three different situations that the REM sleep period has terminated and shifted to the immediately after REM sleep period, that the REM sleep period has not shifted to the immediately after REM sleep period, and that the awakening period has already been reached.

Upon discrimination of the termination of the REM sleep period, an awakening signal is generated upon termination of the REM sleep period to drive an awakening stimulus generating means 24. For the awakening stimulus, there may be employed a sound stimulus, aromatic stimulus of mint series fragrance or the like known to have awakening effect, optical stimulus, and vibratory stimulus, respectively alone or in combination. When the sound or optical stimulus is employed, it is preferable to have the level of stimulus gradually increased, but the initial sound stimulus may be set relatively lower since the sound stimulus has higher awakening effect in the immediately after REM period.

Upon discrimination of the awakening period, the provision of the awakening stimulus either before or just at the set time Tw, the timing of which is made selectable, and it is preferable that the system allows the user to perform this selection upon time setting with the time setting means 20. Further, it is considered that, in the awakening stimuli, the sound stimulus is a strong one having relatively high effect while the optical or aromatic stimulus is a weak one. It is also effective, therefore, to provide the weak stimulus increasing from the time Tp and thereafter the strong stimulus at an optimum time for giving the awakening stimulus, that is, in two steps. This will make it possible to provide to the user an excellently comfortable awakening feeling when, in particular, the immediately after REM sleep period has not been reached between the time Tp and the time Tw, in which event the increasing weak stimulus is given in the NREM and REM sleep periods and the strong stimulus is given when the time Tw is reached, so that the sleep will be gradually led to be shallower and then the comfortable awakening can be realized.

It may be possible, on the other hand, that the user falls asleep again even after the awakening stimulus is given. The present system is provided, therefore, with a resleep judging means 25, so as to judge whether or not the user is falling asleep again. That is, the resleeping judging means 25 carries out the same processing as in the sleep-onset time presuming means 15, so that an event where the pulse rate H(t) shows a decreasing tendency or an average pulse rate for a predetermined period of time becomes smaller than the reference pulse rate will be judged to be falling asleep again. When such state is judged to be present, the awakening stimulus generating means 24 is continuously or intermittently actuated to provide the strong stimulus so as to have the awakening state reached reliably.

Figure 6:
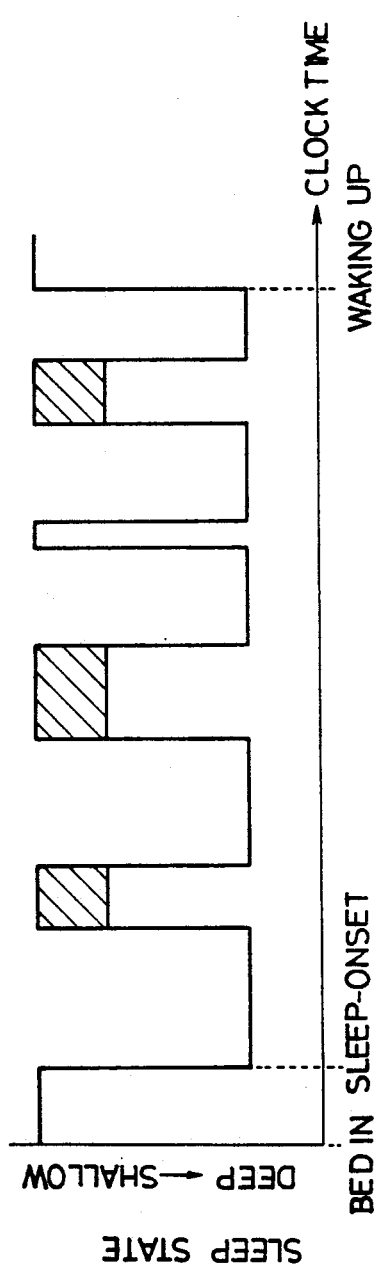
FIG. 6 is a diagram showing an example of the sleep state discriminated in the system of FIG. 1.

Further, the sleep index S(t) obtained at the sleep state discriminating means 22 is stored at a sleep state memory means 26 to which such output means 27 as a display, printer or the like device is connected. After the waking-up, therefore, the user can be furnished by the output means 27 with such a sort of sleeping diagram as shown in FIG. 6. It may also be possible to employ a voice output device for the output means 27 to have the stored data audibly announced.

Figure 7:
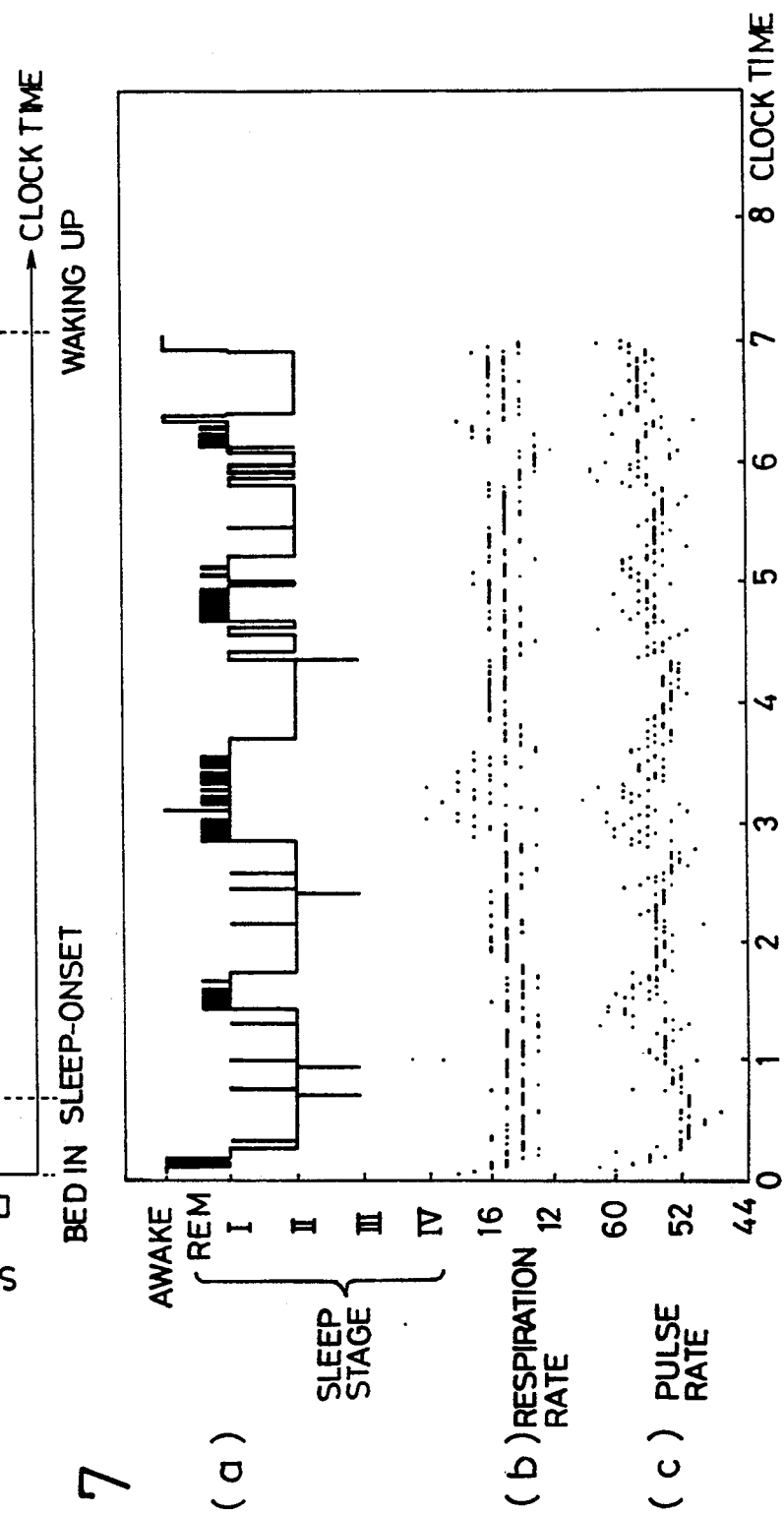
FIG. 7 is a diagram showing changes of the biological signals and the sleep state.

While in the foregoing embodiment an example of employing the pulse rate easily available has been referred to, it is likewise possible to employ the respiration rate as the biological signal since, as will be clear when FIG. 7 is referred to, the respiration rate shown by graph (b) and the pulse rate shown by graph (c) in FIG. 7 change in the same manner in respect of the sleep state.

What is claimed is:

1. A system for discriminating a sleep state of and selectively waking a subject, the system comprising means for setting a measuring time, means for measuring, as a biological signal of the subject, at least one biological signal per unit time selected from the group consisting of pulse rate and respiration rate, a variation index computing means for providing variation indexes $C(t)$ representing variation of the biological signal $H(t)$ in the form of a linear combination of first variation amount $I(t)$ denoting a tendency of increment in time series of said biological signal $H(t)$ from a starting time of the measuring to a time when the biological signal is obtained with second variation amount $D(t)$ denoting a standard variation of the biological signal $H(t)$ during said measuring time, and a sleep index operating means for providing sleep indexes allowing a NREM sleep state and all other sleep states to be discriminated from one another on the basis of said variation indexes $C(t)$ continuously exceeding a predetermined threshold $C(th)$.

2. A system according to claim 1, which further comprises means for setting a reference value $H(r)$ which can be regarded as said biological signal at a stably resting and awakening state on the basis of the biological signal $H(t)$ at initial stage of the measurement, and means for presuming a sleep-on set time when the biological signal is below said predetermined threshold $C(th)$ set on the basis of said reference value $H(r)$.

3. A system according to claim 2, which further comprises a sleep state discriminating means which discriminates, when said variation index $C(t)$ denotes a period other than said NREM sleep period when the biological signal $H(t)$ is above said reference value $H(r)$.

4. A system according to claim 1, wherein said variation index computing means comprises means for obtaining a trend line $Tr(t)$ denotes a trend of the variation with elapsing time on the basis of a moving average $A(t)$ of said biological signal $H(t)$, said trend line being obtained in such that a first rhythm curve $R1$ is obtained with the minimum values of the moving average $A(t)$ at every unit time in respect of passing direction of time, a second rhythm curve $R2$ is obtained with the minimum values of the moving average $A(t)$ at every unit time in respect of receding direction of time and the larger value between the first and second rhythm curves $R1$, $R2$ at each time is plotted as a point of the trend line $Tr(t)$.

5. A system according to claim 3, which further comprises means for generating an awakening stimulus to be given to the user, means for setting an awakening time, and means for controlling operation of said awakening stimulus generating means.

6. A system according to claim 5, which further comprises means for judging a state of resleeping on the basis of said biological signal $H(t)$ measured after an actuation of said awakening stimulus generating means and actuating again the awakening stimulus generating means.

7. A system for discriminating a sleep state of and selectively waking a subject, the system comprising means for setting a measuring time, means for measuring as a biological signal of the subject at least one biological signal per unit time selected from the group consisting of pulse rate and respiration rate, a variation index computing means for providing variation indexes $C(t)$ representing variation of the biological signal $H(t)$ in the form of a linear combination of first variation amount $I(t)$ denoting a tendency of increment in time series of said biological signal $H(t)$ from a starting time of the measuring to a time when the biological signal is obtained with second variation amount $D(t)$ denoting a standard variation of the biological signal $H(t)$ during said measuring time, said variation index computing means for performing a regression operation on said biological signal, and a sleep index operating means for providing sleep indexes allowing a NREM sleep state and all other sleep states to be discriminated from one another on the basis of said variation indexes $C(t)$ continuously exceeding a predetermined threshold $C(th)$.

* * * * *